(12) United States Patent
Schaupp et al.

(10) Patent No.: US 6,770,030 B1
(45) Date of Patent: Aug. 3, 2004

(54) DEVICE FOR CONDUCTING IN VIVO MEASUREMENTS OF QUANTITIES IN LIVING ORGANISMS

(76) Inventors: Lukas Schaupp, Peinlichgasse 6, Graz (AT), A-8010; Thomas Pieber, Med.Uniklinik, Auenbruggerp 15, Graz (AT), A 8036

(*) Notice: Subject to any disclaimer, the term of this patent is extended or adjusted under 35 U.S.C. 154(b) by 0 days.

(21) Appl. No.: 10/088,396
(22) PCT Filed: Sep. 18, 2000
(86) PCT No.: PCT/AT00/00247
§ 371 (c)(1), (2), (4) Date: Mar. 18, 2000
(87) PCT Pub. No.: WO01/21064
PCT Pub. Date: Mar. 29, 2001

(30) Foreign Application Priority Data

Sep. 17, 1999 (AT) .............................. 1594/99

(51) Int. Cl.[7] ................................ A61B 5/00
(52) U.S. Cl. .................. 600/309; 600/365; 600/373
(58) Field of Search ................. 600/309–310, 600/316, 322, 325, 327, 344, 365, 373

(56) References Cited

U.S. PATENT DOCUMENTS

| | | | |
|---|---|---|---|
| 4,622,974 A | 11/1986 | Coleman et al. | |
| 5,237,993 A | * 8/1993 | Skrabal | ....................... 600/309 |
| 5,299,571 A | 4/1994 | Mastrototaro | |
| 5,390,671 A | 2/1995 | Lord et al. | |
| 5,462,645 A | 10/1995 | Albery et al. | |
| 5,568,806 A | 10/1996 | Cheney, II et al. | |
| 5,586,553 A | 12/1996 | Halili et al. | |
| 5,779,665 A | 7/1998 | Mastrototaro | |
| 6,019,728 A | * 2/2000 | Iwata et al. | .................. 600/486 |
| 6,259,937 B1 | * 7/2001 | Schulman et al. | ........... 600/345 |

FOREIGN PATENT DOCUMENTS

WO    WO91/15993    10/1991

OTHER PUBLICATIONS

Fraser, D. (1997) "Biosensors in the Body", Wiley, p. 199f. (to follow).
Jobst, G et al. (1996) Thin–Film Microbiosensors for Glucose–Lactate Monitoring, *Anal. Chem.* (68) 18, pp. 3173–3179. (to follow).

* cited by examiner

*Primary Examiner*—Mary Beth Jones
*Assistant Examiner*—Matthew Kremer
(74) *Attorney, Agent, or Firm*—Collard & Roe, P.C.

(57) ABSTRACT

In a device (10) for in-vivo measurements of quantities in living organisms that comprises a catheter-like tube (11) receiving in a removable manner a setting needle (14) provided for inserting the tube in the organism, with at least one aperture (12) being provided in the wall of the tube (11); and a sensor (18) for detecting the quantity to be measured in the interior of the tube; the sensor (18) is mounted on a separate oblong carrier (17) whose cross sectional dimensions are smaller than those of the interior of the tube. After the setting needle (14) has been pulled out of the tube (11), the sensor can be inserted in said tube (11).

8 Claims, 5 Drawing Sheets

DEVICE FOR CONDUCTING IN VIVO MEASUREMENTS OF QUANTITIES IN LIVING ORGANISMS

CROSS REFERENCE TO RELATED APPLICATIONS

Applicants claim priority under 35 U.S.C. §119 OF Austrian Application No. 1594/99 filed Sep. 17, 1999. Applicants also claim priority under 35 U.S.C. 365 of PCT/AT00/00247 filed Sep. 18, 2000. The international application under PCT article 21(2) was not published in English.

The invention relates to a device for carrying out in-vivo measurements of quantities in living organisms, comprising a catheter-like tube that accommodates, in a removable manner, a needle that is provided for inserting the tube in the organism; at least one opening in the wall of the tube; and a sensor for detecting the quantity to be measured in the interior of the tube.

It is frequently necessary in many areas in the field of medicine and in comparable fields to measure in a repeated or continuous manner concentrations or compositions of body fluids primarily for the purpose of being able to detect disorders of the homeostasis and to be able to treat such disorders, if necessary. For example, diabetes mellitus is a disorder of the metabolism that is reflected by various symptoms, whereby it is possible to control the concentration of the blood glucose by a therapy with insulin. Although this therapy with insulin substantially promotes the well-being of the patient, it is not possible to prevent late complications such as, for example premature blindness, heart and kidney failure, or neuropathies in most cases, but only to delay such complications. One of the most important causes for the late consequences of this disease is the not optimal coordination of the insulin injections with the blood glucose. Therefore, so as to be able to adapt the insulin injections to the needs of the body as required, the glucose concentration has to be measured repeatedly (or continuously) in a precise manner.

All kinds of different methods have been proposed for measuring the glucose in the organism, including blood sugar-measuring devices; non-invasive measuring methods; indirect determination of the glucose via other body parameters; or measurement of the glucose in body fluids other than the blood, for example in the sputum, in the perspiration, or in the urine. Because of the problems encountered when measurements are taken in such fluids, quantification of the glucose in the fluid of the tissue, which is closely connected with the plasma glucose, has been increasingly given more attention in the last few years. Problems arising in the blood such as, for example coagulation, the risk of infection, or protein loading, are highly reduced in this connection if they cannot be avoided, to begin with.

Various possibilities for measuring the glucose in the fluid of the tissue in a continuously manner have been proposed as well:

(1) Minimally invasive sampling methods such as the open micro-perfusion technique, the micro-dialysis, or the ultra-filtration technique.

(2) Sensors that are directly inserted in the tissue; or (3) Techniques by which the tissue fluid is collected through the skin (the so-called suction technique, inverse iontophoresis).

In addition to the open micro-perfusion method and micro-dialysis, sensors that are directly inserted in the tissue have been found to be particularly well-suited for a continuous measuring system.

In connection with the open micro-perfusion technique and micro-dialysis, perfusion of a catheter inserted in the tissue is carried out with a rinsing liquid that, in connection with the open micro-perfusion method, mixes with the fluid of the tissue, whereas in connection with micro-dialysis, an exchange takes place via a membrane. This membrane, on the one hand, permits that the exchange of molecules between the tissue fluid and the rinsing liquid can be controlled in a selective manner; on the other hand, this property is altered by the deposits of endogenous substances (predominantly of proteins, but also of cells). Such deposits go hand in hand with a change in the transport properties of the molecules via the membrane, which is reflected by a diminished concentration of the molecules in the rinsing liquid. This drawback can be circumvented by macroscopic perforations in connection with the open micro-perfusion technique.

The equilibration between the fluid of the tissue and the rinsing liquid is a function of the exchange area and the flow rate of the rinsing liquid. If the flow rate is infinite, complete equilibration between the two liquids takes place. Because of the low flow rate, two decisive drawbacks ensue for the measurement of the substances in the rinsing liquid: firstly, the amount of fluid collected per unit of time is very small, and secondly, the delay caused by the length of the hose (system delay) will increase accordingly.

A higher flow rate is frequently selected for that reason in order to make more liquid available more rapidly. The drawback of this mode of operation consists in the not-complete mixing of the two liquids, which, if possible, has to be compensated by measuring other parameters. This causes additional requirements that the measuring technique needs to satisfy, which is found to be difficult particularly in connection with on-line measurements.

In addition to the sampling methods, which permit an ex-vivo measurement (sensor is located outside of the body), proposals already exist for in-vivo measurements, whereby the sensor is directly inserted in the tissue. In addition to the higher requirements the sensor needs to meet with respect to bio-compatibility, mechanical stability and size, it is necessary to pay attention to the problem posed by the calibration of the sensor. Although the sensors exhibit very good in-vivo characteristics, characteristics are observed that are changed in vivo. In order to take such changes into account, different starting points exist: a frequently employed starting point is the calibration of the sensor value against one or more blood values, whereby it is implicated that, in the case of a glucose measurement, the concentration of the glucose in the fluid of the tissue is equal to the concentration in the blood. So as to be able to render this a correct statement, the concentration of the glucose has to be in a state of equilibrium between the blood and the fluid of the tissue because a shift in terms of time exists between these two compartments. In addition to the painful stress affecting the person involved, calibrating changes "away" (for example infections in the tissue, encapsulation of the sensor) constitutes a substantial shortcoming of this measurement.

So as to avoid the drawbacks of the sampling methods (time delay), incomplete equilibration, a membrane disposed in between) and the implanted sensor (no calibration possibility, mechanical stability), a sensor (e.g. a glucose, lactate or glutamate sensor) can be inserted in a specially shaped catheter or general a tube or hose, and inserted in the tissue with the help of such a catheter or tube or hose); compare, for example U.S. Pat. No. 5,299,571 A, or U.S. Pat. No. 5,568,806 A. The catheter has a macroscopic opening, so that an exchange can take place between the fluid of the tissue and the sensor. After the sensor has been inserted in the respective tissue with the help of a setting needle present in a lumen, said setting needle is removed from the catheter. The setting needle or the associated lumen take up a mayor portion of the cross section of the catheter, and the sensor is arranged in a fixed manner in the lumen located adjacent to the lumen receiving the setting needle. The aforementioned opening in the catheter tube is located adjacent to the sensor. Suitable conduits lead from said sensor to the outside in order to permit a connection to an electronic measuring system. The manufacture of the catheter tube requires relatively much expenditure because of the two special lumens, whereby, furthermore, a relatively large cross section, notably the one receiving the setting needle, cannot be used for carrying out the measurement and has to be viewed as a lost volume.

Other types of catheter systems have already been proposed—compare, for example U.S. Pat. No. 5,779,665 A; U.S. Pat. No. 5,586,553 A; or U.S. Pat. No. 5,390,671 A, whereby the setting needle is present there outside of the catheter tube, approximately parallel with said catheter tube (U.S. Pat. No. 5,779,665 A), or with inclusion of the catheter tube. This entails drawbacks when the catheter is set such as, for example the impermissible fact that the catheter tube is being taken along via a thread (U.S. Pat. No. 5,779,665 A1), or causes pain when the relatively thick unit comprising the setting needle and the catheter tube is inserted. In connection with such known arrangements, the sensor is present in the remaining catheter tube, whereby it has been proposed also (compare U.S. Pat. No. 5,390,671 A) to mount the sensor in a displaceable manner in a rigid, strip-shaped carrier in the catheter tube, said carrier being bent at a right angle.

In connection with the last-mentioned embodiments, a set of setting utensils is provided or required for setting the catheter with the sensor in place. This entails additional expenditure.

Now, the problem of the invention is to provide a measuring system of the type specified above that permits working with the smallest of cross sections when the catether-like protective tube is set in place, so that the catheter or the catheter-like tube can be set in a simple manner and largely without causing pain, whereby, furthermore, no set of setting utensils and no trained personnel are needed, but self-application is made possible instead.

The device as defined by the invention of the type specified above is characterized in that the sensor mounted on a separate, oblong carrier as it is known per se, the cross sectional dimensions of which are smaller than the ones of the interior of the tube, and can be inserted in said tube after the setting needle has been pulled out of the tube.

In connection with the present device, therefore, the lumen of the catheter-like protective tube is used in two ways, so that no second lumen is required (for the sensor). In the preferably only one lumen of the tube, the setting needle is accommodated first by inserting it in the tissue with the help of the tube. The setting needle is subsequently pulled back, which releases the lumen of the tube, in order to then insert the sensor with the help of a carrier. The carrier, of course, has to possess a certain rigidity in order to permit such insertion in the catheter-like tube, even though a certain flexibility of the carrier is entirely possible and advantageous as well. This technique permits a minimal cross section of the tube with the sensor finally accommodated therein, and it is possible also to directly measure the respective quantity such as, for example glucose etc. After the tube has been set in place, it is possible also in this connection to replace the sensor without requiring another piercing, i.e. setting of the catheter.

Furthermore, owing to the fact that the sensor carrier has smaller cross sectional dimensions than the lumen of the tube, a space is created between the catheter tube and the carrier or sensor, through which liquids can be introduced from the outside. Preferably, provision is made in this connection that a channel having a generally ring-shaped cross section for a rinsing or calibration liquid or the like is formed between the sensor carrier in the installed condition, and the inner wall of the tube.

The admitted liquids per se may assume different functions as follows:

(1) The liquid contains the substance to be measured and may therefore serve as the calibration medium (e.g. Ringer solution with 5 mmols/liter addition of glucose for calibrating glucose sensors;

(2) due to an increased high speed of the liquid, it is possible to remove deposits on the sensor, i.e. to flush such deposits away;

(3) it is possible to add substances to the liquid in order to cause different effects such as, for example buffers for a constant pH, high-oxygen agents against an oxygen deficit in the tissue, infection-inhibiting agents, increase of the permeability, or substances lowering the blood sugar (e.g. insulin).

Of primary importance in this connection is the—periodic—calibration of the measuring device with the help of a channel formed in the passage between the sensor carrier and the wall of the tube, and likewise the periodic rinsing, which is useful for obtaining an exact measurement.

However, it is particularly advantageous if the separate sensor carrier has the shape of the tube because if the carrier of the sensor is realized in the form of a tube (and the sensor is positioned on the outer side of the tube), it is possible—due to the inner lumen of the carrier tube—to additionally introduce in an advantageous manner a medication, for example insulin, if such a substance may not come into any direct contact with the sensor.

For an increased feed of said substance or substances, it is advantageous also in the present case if the tubular sensor carrier has at least one opening in its wall that is positioned adjacent to its open distal end.

In order to prevent the substance from flowing back into the space between the sensor carrier and the catheter tube and to thereby safely avoid any direct contact of the substance with the sensor, it is favorable, furthermore, if a ring seal providing sealing against the inner wall of the catheter-like tube is arranged on the tubular carrier in a site located between the open distal end or, if need be, the opening in the wall of the tubular sensor carrier, on the one hand, and the sensor on the other. Therefore, if a seal is thus mounted between the tip of the carrier and the sensor, the substance can exit only into the tissue.

Therefore, it is overall possible with the embodiment of the device as defined by the invention to measure directly on site, and the sensor can be calibrated and "maintained". Furthermore, active substances can be introduced for the measurement, and it is possible also to feed substances into the tissue in response to the measuring result by penetrating the tissue only once.

When the sensor is directly inserted in the tissue, the ambient temperature is preset by the body temperature, which is relatively constant. Therefore, a measurement of the temperature as it is required in connection with ex-vivo measurements, can be omitted. By omitting the pumping devices, which are required in connection with sampling methods for ex-vivo measurements, the structure of the device is substantially simplified, which reduces the costs. Hose pumps are employed, as a rule, in connection with sampling methods because different directions of flow can be synchronized with such pumps, whereby most of the energy is consumed with such type of pumps for deforming the pump hoses, so that the consequence is a very poor degree of efficiency (which is critical in particular in conjunction with portable devices). Since it is possible in connection with the device as defined by the invention to employ injector pumps for feeding calibrating or rinsing liquid, or active and therapeutic substances, the operation of the system, furthermore, requires less energy.

Moreover, by omitting suction pumps, no dilution of the tissue fluid by a rinsing or calibrating solution liquid will occur with the device as defined by the invention in normal measuring operations, which means that a completely equilibrated solution is available on the sensor. This also means, furthermore, that it is no longer necessary to determine the re-finding rate. Since no tissue fluid is extracted from the body permanently, the tissue fluid cannot become poor around the catheter. The only consumption of tissue fluid takes place directly on the sensor; however, such consumption is negligible.

For the intensive, safe contact of the sensor with the tissue fluid, it is also advantageous in this connection if the wall of the catheter-like tube has several openings successively located one after the other in the axial direction within the area of the sensor. In this way, tissue fluid can flow to the sensor through a number of openings, i.e. macroscopic perforations in the wall of the catheter tube, which, furthermore, means that the given position of the sensor is relatively uncritical, so that when the carrier with the sensor is pushed into the catheter-like tube, no exact positioning of the sensor has to be achieved after the setting needle has been pulled back.

In order to safely avoid any damage to the sensor by rubbing on the inner wall of the catheter-like tube when the carrier with the sensor is pushed into the catheter-like tube, the aim should be that the sensor has the smallest possible dimensions in the radial direction, i.e. the sensor should project from the carrier as little as possible. Accordingly, it is advantageous if the sensor is produced by application of the thin-film technology or silicon technology, as it is known per se. Furthermore, it is favorable for this purpose as well if the sensor is at least partially embedded in the carrier. In this connection, the sensor may have an expanse in the longitudinal direction of the carrier that is greater than it is usually the case, which is particularly advantageous if the catheter-like tube has a plurality of apertures.

The measuring principle of the sensor is known per se and may consist of physical and chemical methods as well as also combinations of the two methods. For example, an electrochemical measurement is suitable for the determination of the substance. According to current practice, an amperometric method with constant polarization voltage for the quantification is particularly well-suited in this connection (see U.S. Pat. No. 5,462,645 A). In this process, an enzyme (e.g. glucose oxidase, glutamate oxidase, lactate oxidase, etc.) is converted according to a chemical reaction into hydrogen peroxide, which is oxidized on an electrode by the constant polarizing voltage. The quantity of the sensor current generated in this process is dependent upon the concentration of the substance to be determined. The following applies by way of example to glucose measurements:

$$Glucose + O_2 \xrightarrow{Glucoseoxidase} Gluconic\ Acid + H_2O_2$$

$$H_2O_2 \xrightarrow{+600\ mmV} O_2 + 2H^+ + 2e^-$$

Various technologies are available for the manufacture of the sensors (see, for example FRASER, D.: Biosensors In The Body. Wiley 1997, page 199f). A technique commonly employed at the present time would be also the thick-film technology, by which is it possible to realize structures of 0.1 mm. However, with the thin-film technology, it is possible to obtain structures in the $\mu$m-range, and with the silicon-technology it is possible to build sensors even in the sub-$\mu$m range. Since the invasiveness of the system increases with the increase in the diameter, it is important that the sensor has small dimensions in the radial direction. Especially the thin-film technology or the silicon technology are well-suited for that reason for realizing the sensor. So that the volume required for the sensor can nonetheless be made available, the sensor can be expanded in the axial direction, as mentioned before. A sensor comprising a size and technology that could be considered for realizing the present measuring system is represented by the sensor described by JOBST G ET AL in: Thin-Film Microbiosensors For Glucose-Lactate Monitoring, Anal. Chem. (68) 18, pp 3173–3179, 1996.

An embodiment of the catheter that is feasible within the framework of the invention, comprises perforating (by means of a laser beam or using a mechanical drill) a commercially available vein-dwelling cannula. Various sizes of the catheter are possible, whereby the outside diameter may be in the range of from 0.6 mm to 2.0 mm. The diameter of the carrier for the sensor can be adapted to the inner tube, so that the sensor mounted on the surface of the carrier can be inserted in the catheter without any problems. With the smallest embodiment of the arrangement (outside diameter of the catheter=0.6 mm; diameter of the carrier=0.3 mm), which conforms to the size of the needle of an insulin pump, the radial expanse of the sensor may amount to 0.15 mm at the most. These dimensions can be realized without any problem with the aforementioned technologies, primarily with the thin-film and the silicon technologies.

Finally, for safety reasons, i.e. in order to safely exclude any damage to the connection cables and to the sensor as well, it is advantageous, furthermore, if the sensor is connected to electrical cables that are embedded in the carrier.

The invention is explained in the following in greater detail with the help of preferred exemplified embodiments shown in the drawings. However, the invention is not limited to such exemplified embodiments. In detail, the drawings show the following.

Figure 1:
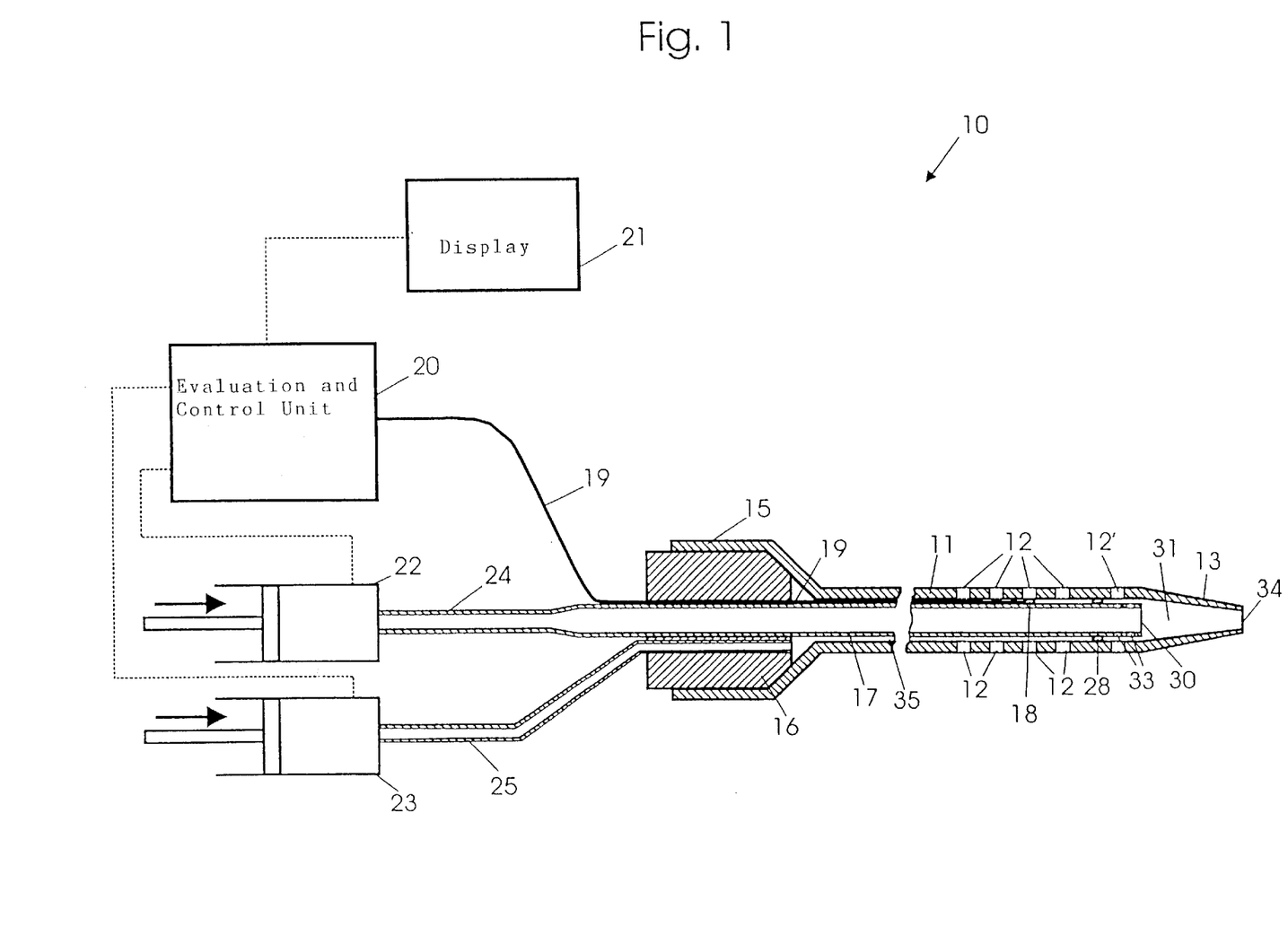
FIG. 1 is a schematic representation of a measuring device as defined by the invention.

FIG. 1 shows by a schematic representation a device for carrying out in-vivo measurements of quantities in living organisms. Said measuring device as a whole is denoted by 10 and comprises a catheter-like tube, or protective tube, simply referred to in the following as the catheter 11. The selection of the material of said catheter 11 can be based on the experience gained with currently employed vein-dwelling catheters or vein-dwelling cannulas with respect to bio-compatibility, strength, sliding ability, size etc. In its front area, the catheter 11 is provided with the macroscopic apertures 12, which may have a diameter, for example in the order of magnitude of 0.2 to 0.5 mm. At its front, distal end 13, the catheter 11 is pointed in order to conform in this way to an originally inserted setting needle 14 (see FIG. 2A). At its rear, i.e. proximal end, the catheter 11 is provided with a widening 15 in order to receive in said widening a stopper-like base 16 for a tubular, oblong sensor carrier 17. On its outer side near its front, distal end, said carrier 17 supports a sensor 18 drawn only schematically. In the condition in which the catheter 11 is in place in a tissue (not shown) as shown in FIGS. 1 and 3, said sensor is located in the area of the apertures 12. Via the connection cables 19, the sensor 18 is connected to the measuring electronics, concretely to an evaluation and control unit 20, which per se is structured in the conventional manner and needs not to be explained here in greater detail. A display unit 21 is connected to said evaluation and control unit 20. Furthermore, from said evaluation and control unit 20, control lines may lead to pumps, for example to the injector pumps 22, 23. With the help of such pumps, liquids can be pumped through the interior 32 (see FIG. 3) of the tubular carrier 17 and the ring-shaped channel 35 located between the carrier 17 and the catheter 11—see also the lines 24 and 25. This is explained in greater detail farther below.

Figure 2A:
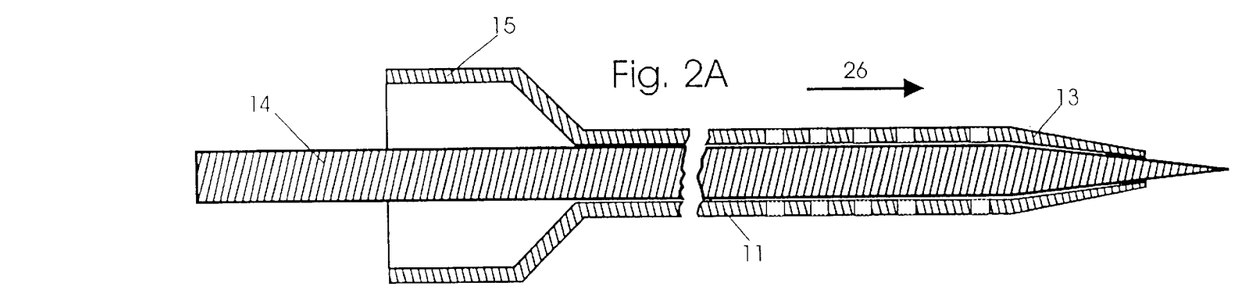
FIGS. 2A, 2B and 2C show the successive phases involved when the catheter-like tube of the present measuring device is placed in position with the help of a setting needle (see FIG. 2A), whereby the setting needle is then pulled back (see FIG. 2B), and a carrier supporting a sensor is then finally pushed into the catheter-like tube (see FIG. 2c).
Figure 2B:
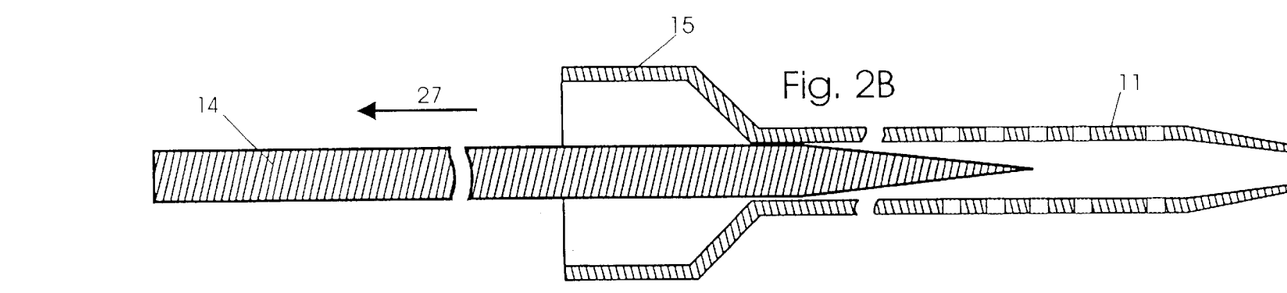
Figure 2C:
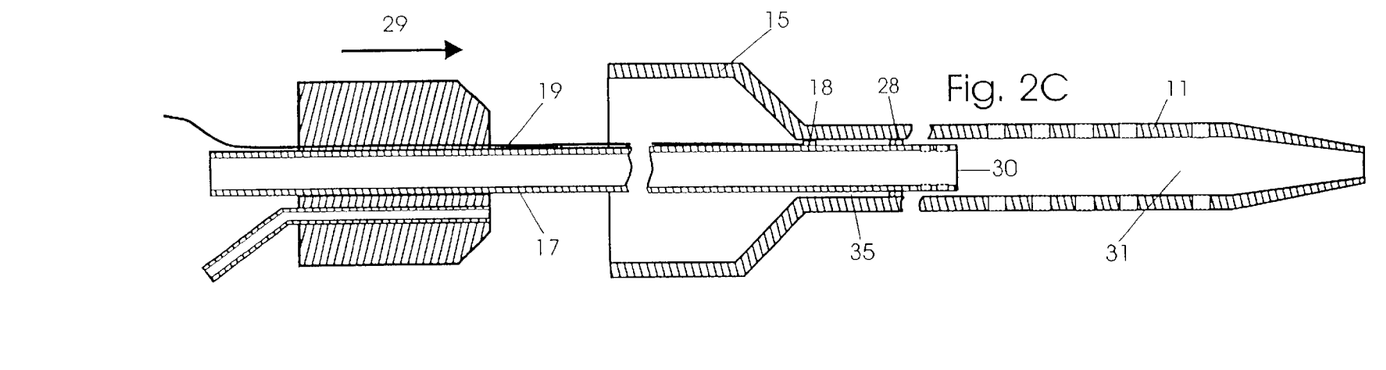
Figure 3:
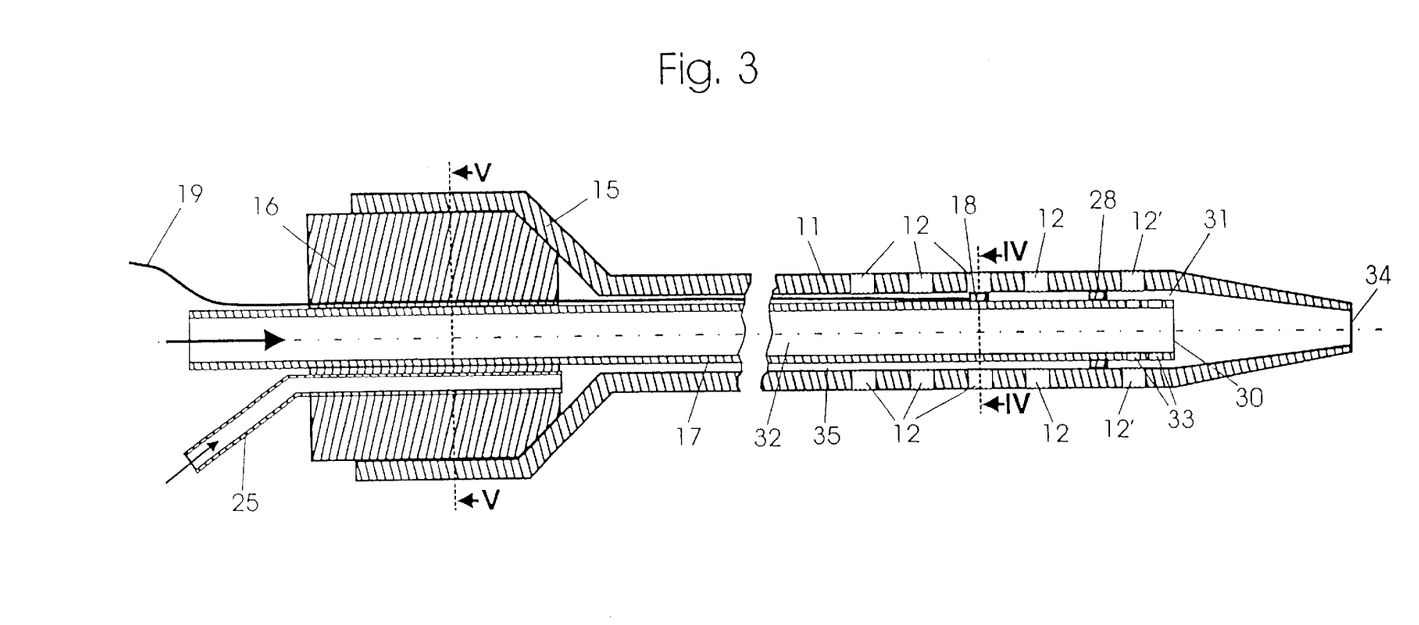
FIG. 3 shows an axial section through the catheter-like tube with the sensor mounted on the carrier installed in said tube, on a scale enlarged versus FIG. 1.
Figure 4:
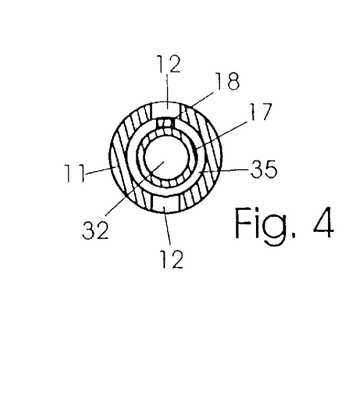
FIGS. 4 and 5 show cross sections according to the section lines IV—IV and V—V in FIG. 3.

As shown in FIG. 2A, the catheter 11 is inserted in the tissue with the help of the setting needle 14—see the arrow 26 in FIG. 2A, whereby the distal end 13 of the catheter 11—as mentioned before—ends with a conical shape for the purpose of simplifying the insertion process. After the catheter 11 has been placed in position in the tissue, the setting needle 14 is pulled back—see the arrow in FIG. 2B—and subsequently replaced by the tubular carrier 17 for supporting the sensor 18, for the connections 19 of the sensor 18, and for a seal 28 that may be realized in the form of a sealing ring. This insertion movement of the carrier 17 is indicated in FIG. 2C by an arrow 29. The distal end 30 of the carrier 17, which is simply referred to in the following as the inner tube, and which is open, is formed by the catheter 11—compare also FIGS. 1 and 3 in addition to FIG. 2C. The proximal part of the original lumen of the catheter 11 is separated from the distal part by the seal 28. The distal part, which is referred to here as the lumen 31, is thus forming a new lumen, namely the ring-shaped channel 35.

In order to increase the outlet area of the lumen 32, which is formed by the inner tube 17, the additional perforations 33 are provided in the inner tube 17 near the distal end of the latter. The purpose of enlarging the outlet area is to make clogging of the inner tube 17 more difficult because it is possible that tissue particles may have penetrated the catheter lumen 31 through the distal face side 34 of the catheter 11, or through the front-most perforations provided on the catheter 11. If the device is correctly applied, a substance, and in particular a medication, for example insulin, can be admitted into the lumen 31 formed by the catheter 11 through the inner tube 17, and can be passed on from said lumen into the tissue by way of the distal face side 34 and possibly through the front-most perforations 12'. Such a medication can be (but does not have to be) supplied in response to the measurement taken by means of the sensor 18.

Figure 5:
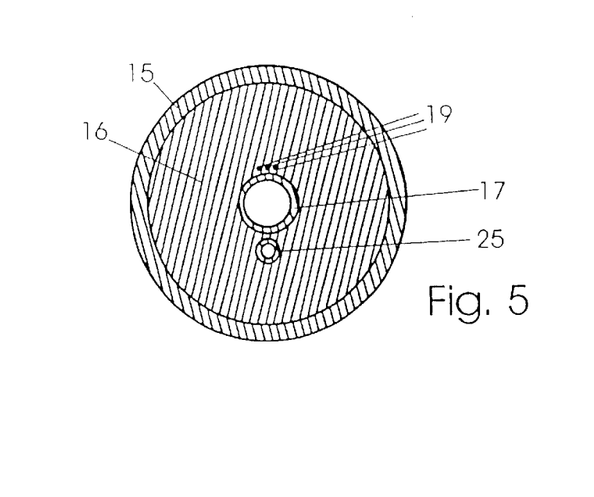

According to FIGS. 1 to 4, the sensor 18 is mounted on the surface (outer side) of the inner tube 17. The connection lines 19 of the sensor 18 may be simply installed on the surface of the inner tube 17, or may be embedded in the latter (compare FIGS. 5 and 6). Said connecting lines 19 are installed extending through the base 16 for the inner tube 17, and lead to the evaluation and control unit 20. The base 16 can be either screwed to or plugged (clamped, for example by means of a Luer adapter) into the catheter 11, i.e. the widening 15 of the latter.

Via the perforations 12, the sensor 18 is communicatively connected with the tissue fluid. Preferably, the sensor 18 is directly located under one of the apertures 12 in order to keep the distance of migration of the tissue fluid as short as possible. Another tube for rinsing and calibrating liquids serving as the conduit 25 is extending through the base 16 for the inner tube 17. Via the ring-shaped channel 35, which is formed by the inner wall of the catheter 11 and the outer side of the inner tube 17, said liquids are received by the sensor 18 and can be directly transferred into the tissue via the apertures 12.

In order to avoid any direct contact of the respective liquid that is admitted via the lumen 32 of the inner tube 17 with the help of the pump 22, with the sensor 18, the seal 28 is mounted between said two spaces for liquid. At the same time, said seal 28 serves as a spacer and guide element when the inner tube 17 is inserted (see FIG. 2C), in order to keep the sensor 18—which is mounted behind it—away from the inner wall of the catheter 11, and to safely avoid in this manner any damage to the sensor 18 while the inner tube 17 is being inserted.

Figure 6:
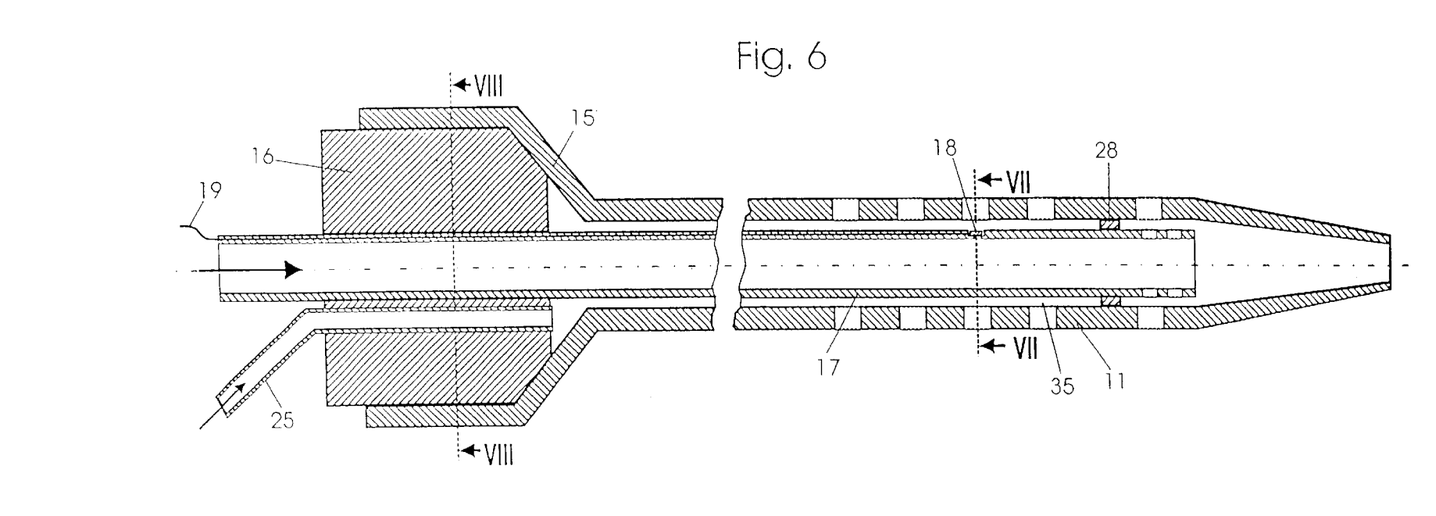
FIGS. 6, 7 and 8 show a modified device conforming to the respective representations in FIGS. 3 to 5, with a longitudinal section (in FIG. 6) and cross sections (in FIGS. 7 and 8), whereby the sensor is arranged in the present case in a recess of the carrier, and whereby the connection cables leading to the sensor are embedded in the carrier.
Figure 7:
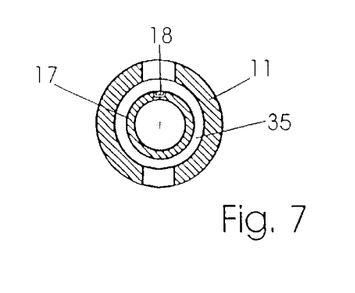

So as to achieve an even higher degree of safety in this regard, provision may be made also—as mentioned before and apart from the embedded connection lines 19 for the sensor 18—to mount the sensor 18 in a recess of the inner tube 17, as it is shown in FIGS. 6 and 7. In all other respects, the embodiment according to FIGS. 6 to 8 corresponds with the one according to FIGS. 1 to 5, so that the description needs not to be repeated.

Figure 8:
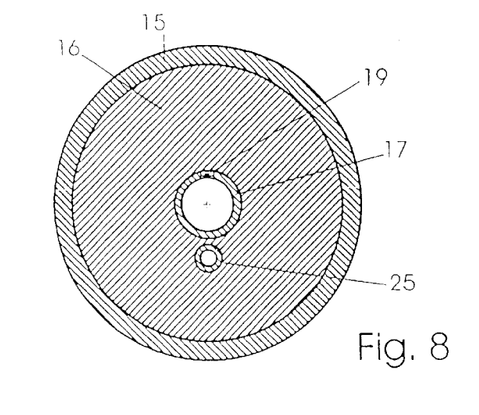

For the sake of completeness, the procedure followed for calibrating the measuring device is explained in greater detail in the following with the help of FIG. 8.

The sensor 18 is calibrated with the help of a calibrating liquid, which is transported to the sensor 18 by way of the channel 35 between the catheter 11 and the carrier (the inner tube) 17. The calibrating liquid contains in this connection a defined, known concentration of the substance to be measured (in connection with a measurement of the glucose, for example a concentration of 5 mmols/liter glucose). The electrical current of an amperometric glucose sensor 18 set in this process can be associated with said glucose concentration. If the sensitivity "E" of the sensor 18 (current change per change in the concentration in nA/mmol/liter) is known, the concentration of the substance of interest here can be calculated backwards based on the measured current. If the sensitivity of the sensor 18 is not known, the sensor 18 has to be calibrated with two calibration liquids having different concentrations. The sensitivity "E" and the zero current $I_0$ of the system can be calculated based on the known difference in concentration and the resulting difference between the two currents of the sensor 18 at said concentrations.

Figure 9:
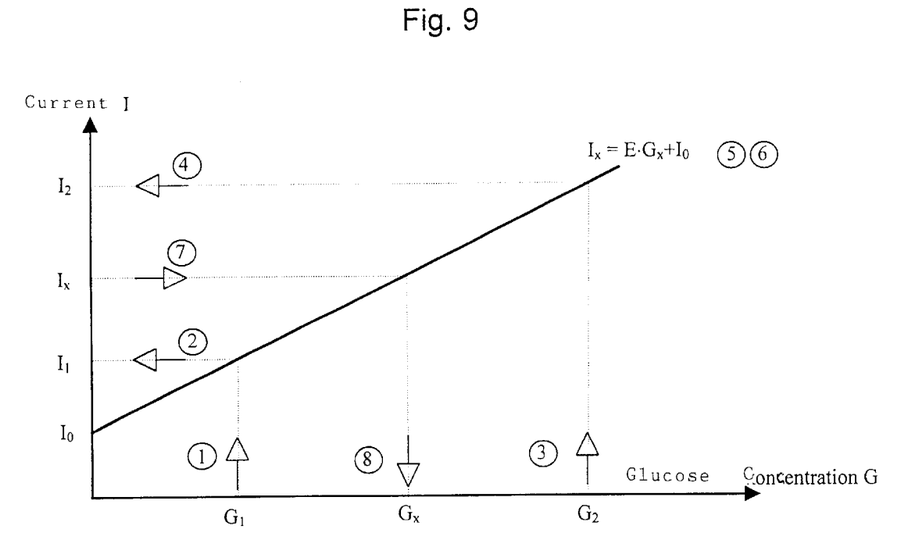
FIG. 9 shows by a diagram the calibration and the measurement processes, using the present measuring device.

FIG. 9 illustrates an example of the calibration of a glucose sensor 18 and the subsequent measurement of the glucose. The arrows in FIG. 9 indicate the direction of the information flow; the numerals 1 to 8 conform to the sequence during the calibration and measurement.

The interrelation between a glucose concentration $G_x$ and the associated, measured current $I_x$ can be generally stated in the linear range as follows:

$$I_x = E \cdot G_x + I_0,$$

where E is the sensitivity E and $I_0$ is the zero current. By calibrating with two different calibration solutions with the —known—concentrations $G_1$ and $G_2$, and the correspondingly determined currents $I_1$ and $I_2$, it is therefore possible to determine the sensitivity E and the zero current $I_0$ as follows:

$$E = (I_2 - I_1)/(G_2 - G_1)$$

$$I_0 = I_1 - E \cdot G_1$$

With knowledge of the sensitivity E and the current zero current $I_0$, it is, in turn, possible to calculate the glucose concentration $G_x$ acting on the sensor 8 by measuring the current $I_x$:

$$G_x = (I_x - I_0)/E$$

From this follows the following procedure for calibrating the system:

(1) Admission to the sensor 18 of the one calibrating medium $G_1$.

(2) Measurement of the associated current $I_1$.

(3) Admission to the sensor 18 of the other calibrating medium $G_2$.

(4) Measurement of the associated current $I_2$.

(5) Calculation of the system parameters $E$, $I_0$.

(6) Testing of the system parameters for their quantity and change.

(7) Measurement of the current $I_x$.

(8) Calculation of the corresponding glucose concentration $G_x$.

If the calibration is carried out at regular time intervals, the operational behavior of the sensor 18 can be determined by changing the sensitivity $E$ and the zero current $I_0$. Changes in the sensitivity $E$ and the zero current $I_0$ may have different causes and consequences: a reduced action of the enzyme; deposits or encapsulation with the body's own substances (protection against foreign bodies). By determining the two quantities ($E$, $I_0$), it is possible to draw conclusions with respect to the cause, and appropriate steps can be implemented accordingly. If a deposit or encapsulation is found to be present, it is possible to flush it away with the calibration liquid and to restore the original sensitivity. If that is unsuccessful, the useful life of the sensor 18 can be estimated based on the reduction in the sensitivity $E$ or the increase in the zero current $I_0$, and it is thus possible to determine the point in time for replacing the sensor 18 in due time.

The in-vivo calibration represents another advantage of the device described above. In such a calibration, the concentrations determined with the device are compared with blood values. The determination, for example of the glucose from the blood is a standard method and is carried out several times each day by the patient himself. If the relation between the two determined values (glucose determined in the blood in relation to the glucose in the tissue fluid) changes, it is possible to infer from such a change a change in the body. The change may be physiological (time delay between the two signals), but also patho-physiological (inflammation around the catheter 11, reaction of rejection, etc.). Furthermore, such changes may be followed by appropriate steps as well (e.g. replacement of the sensor 18; new insertion of the catheter 11; testing of the system).

What is claimed is:

1. The system according to the tubular carrier has at least one opening in its wall located adjacent to an open, distal end thereof.

2. The system according to claim 1, wherein a ring seal sealing against the wall of the catheter-like tube is arranged in a site located between the open, distal end and the opening in the wall of the tubular carrier, on the one hand, and the sensor, on the other hand.

3. The system according to claim 1, wherein the wall of the catheter-like tube has a plurality of apertures successively arranged in an axial direction thereof in the area of the sensor location.

4. The system according to claim 1, wherein the sensor is realized by application of thin-film technology.

5. The system according to claim 1, wherein the sensor is realized by application of silicon technology.

6. The system according to claim 1, wherein the sensor is at least partly embedded in the carrier.

7. The system according to claim 1, wherein the sensor is connected to electrical cables embedded in the carrier.

8. A system for in-vivo measurements of quantities in a living organism, comprising

- a catheter-like tube having a tubular wall with only one single lumen therein and at least one aperture in its tubular wall;
- a removable setting needle for inserting the catheter-like tube in the organism;
- a separate, oblong tubular carrier for applying a medicament, on which a sensor for detecting the quantity to be measured is mounted for insertion in the single lumen of the catheter-like tube, the carrier being sealed against the tubular wall of the catheter-like tube;
- a base for supporting the carrier when inserted in the single lumen, the base being arranged for insertion into an end of the catheter-like tube;
- a line extending through the base for supplying a liquid for rinsing or calibrating the sensor on the carrier;
- the cross sectional dimensions of the carrier and of the setting needle being smaller than the cross sectional dimension of the single lumen, and the single lumen having a cross section adapted for only alternately receiving either the setting needle or the carrier with the sensor, whereby the carrier is in place of the setting needle after replacement of the setting needle with the carrier; and
- the carrier, when inserted in the single lumen being supported by the base inserted at the end of the catheter-like tube, and defining a channel for the liquid substantially having an annular section between the carrier and the wall of the catheter-like tube, the line extending through the base being in flow connection with said annular channel.

* * * * *